(12) United States Patent
Steur

(10) Patent No.: US 8,745,802 B2
(45) Date of Patent: Jun. 10, 2014

(54) DENTAL CLEANING MOUTHPIECE WITH DIFFERENT BRISTLE SECTINS FOR DIFFERENT DENTAL REGIONS

(75) Inventor: Jelte Steur, Delft (NL)

(73) Assignee: Koninklijke Philips N.V., Eindhoven (NL)

( * ) Notice: Subject to any disclaimer, the term of this patent is extended or adjusted under 35 U.S.C. 154(b) by 83 days.

(21) Appl. No.: 13/142,081

(22) PCT Filed: Dec. 4, 2009

(86) PCT No.: PCT/IB2009/055521
§ 371 (c)(1),
(2), (4) Date: Jun. 24, 2011

(87) PCT Pub. No.: WO2010/076695
PCT Pub. Date: Jul. 8, 2010

(65) Prior Publication Data
US 2011/0252590 A1   Oct. 20, 2011

(51) Int. Cl.
*A46B 9/04* (2006.01)
*A46B 13/02* (2006.01)
*A61C 17/22* (2006.01)

(52) U.S. Cl.
USPC .......................... 15/22.1; 15/167.2

(58) Field of Classification Search
USPC ................. 15/22.1, 167.2; 433/216
See application file for complete search history.

(56) References Cited

U.S. PATENT DOCUMENTS

| | | | |
|---|---|---|---|
| 5,175,901 A * | 1/1993 | Rabinowitz | 15/167.2 |
| 5,365,624 A * | 11/1994 | Berns | 15/22.1 |
| 6,223,376 B1 | 5/2001 | Lee | |
| 6,353,956 B1 * | 3/2002 | Berge | 15/22.1 |
| 7,537,451 B1 * | 5/2009 | Ramnarine | 433/216 |
| 2005/0026103 A1 | 2/2005 | Wasylucha | |
| 2007/0009856 A1 | 1/2007 | Jones et al. | |

* cited by examiner

*Primary Examiner* — Randall Chin

(57) ABSTRACT

The mouthpiece carrier assembly (12) is adapted and configured to receive the upper and lower teeth of the user. The mouthpiece carrier assembly is driven such that the bristles mounted on the teeth-facing surfaces of the mouthpiece assembly contact said surfaces and provide a cleaning effect therefor. A plurality of bristle sections (30, 32, 34, 41, 44) are secured to the teeth-facing portions of the mouthpiece assembly, wherein the bristle sections each have bristles which have a particular configuration and are otherwise adapted to provide effective cleaning for an associated dental region.

20 Claims, 1 Drawing Sheet

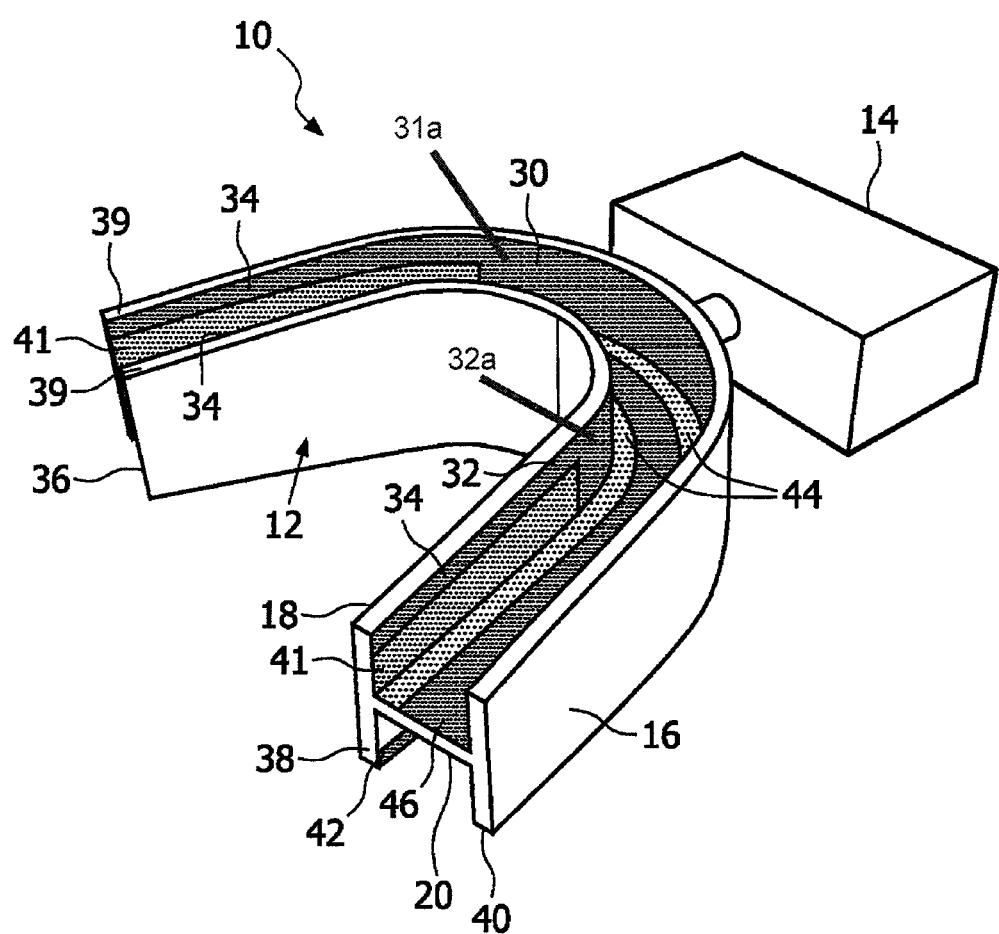

DENTAL CLEANING MOUTHPIECE WITH DIFFERENT BRISTLE SECTINS FOR DIFFERENT DENTAL REGIONS

TECHNICAL FIELD

This invention relates generally to mouthpieces for cleaning teeth, and more specifically concerns such a mouthpiece where the bristles in the mouthpiece are not all the same, but are different in different regions to accomplish different cleaning functions.

BACKGROUND OF THE INVENTION

It is well known that different dental regions of the mouth have different cleaning and/or appearance requirements or goals. Conventional toothbrushes, however, have a single bristle field, so that the selection of particular bristle characteristics is a compromise. Some bristles in a single bristle field can be particularly adapted to clean interproximal areas of the teeth. The effectiveness of interproximal bristles, however, is often limited because the brush is moved throughout the entire mouth by the user. Thus, the position of the interproximal bristles, which are meant to reach between the teeth, are not always aligned with those areas. Having different toothbrushes to accomplish a variety of functions, for cleaning or appearance of particular regions of the teeth, however, is generally considered to be impractical and too time consuming.

Specific to power toothbrushes, particular dental requirements for different regions of the teeth can be met with the use of different brushheads, but it is inconvenient, as well as costly, to constantly change brushheads.

The use of a dental mouthpiece has the potential for accomplishing different cleaning needs with one appliance, thus overcoming the above-described problems of toothbrushes. Historically, however, mouthpieces have used a single type of bristle in the bristle field thereof.

SUMMARY OF THE INVENTION

Accordingly, such a mouthpiece comprises a carrier assembly adapted and configured to receive the upper and lower teeth of the user; a system for driving the mouthpiece carrier assembly such that bristles mounted on teeth-facing surfaces of the mouthpiece assembly contact said surfaces and provide a cleaning effect therefor; and a plurality of bristle sections secured to the teeth-facing portions of the mouthpiece carrier assembly, wherein different regions of the teeth require different cleaning, the bristle sections including bristles having characteristics adapted for cleaning of teeth in said different teeth regions.

BRIEF DESCRIPTION OF THE DRAWINGS

The FIGURE is a perspective view of a mouthpiece incorporating the features of the present invention.

BEST MODE FOR CARRYING OUT THE INVENTION

FIG. 1 shows a dental mouthpiece assembly 10. The mouthpiece assembly 10 includes a mouthpiece carrier 12 which is adapted to receive the upper and lower teeth of the user, and a power and control assembly which is shown generally at 14. The mouthpiece carrier 12 is in the general form of a horseshoe, and typically comprises a plastic material. If the mouthpiece carrier 12 is to receive both the upper and lower teeth, the cross-section of the mouthpiece is in the form of an "H", with two vertical side members 16 and 18 and an intermediate horizontal member 20, as shown in the FIGURE. The side members 16, 18 are typically high enough to cover the side surfaces of the teeth. In some cases, however, the mouthpiece unit 12 covers only the upper or lower teeth, and in that case, the cross section of the mouthpiece unit will be in the form of a "U", either upright or upside down, depending upon whether the appliance is for the upper or lower teeth.

On the interior (teeth facing) surfaces of the side members 16, 18, and on the upper and lower surfaces of horizontal member 20, are positioned bristles or other members designed for scrubbing the teeth or other dental cleaning action. Typically, these bristles are the same over the entire area of the mouthpiece, thereby providing a similar cleaning action for all of the teeth or other dental regions, such as the gum line or the interproximal areas.

In the present invention, however, different regions of the mouthpiece 12, covering different dental regions, have different bristles. Since the bristle arrangement will be similar between the upper and lower portions of the mouthpiece unit, the bristle arrangement will be only described herein with respect to the upper portion of the mouthpiece, which accommodates the upper teeth of the user.

The bristles may be attached to the various interior surfaces of the mouthpiece unit in various ways, including stapling, glued or molded into the mouthpiece. As will be seen in more detail, the individual bristles can vary in cross-sectional shape, cross-sectional surface area and diameter, length, material density, angle and configuration spacing and shape, even color, to accomplish specific cleaning goals. Generally, in conventional toothbrush/mouthpiece applications, the bristles will be 0.01-0.08 mm in diameter, with a filament length of 1-5 mm and a circular cross-section. In the present embodiment, the various regions have bristles with particular characteristics to accomplish particular functions.

In the FIGURE, region 30 covers the front six teeth and can include bristles which are particularly adapted for whitening or polishing. Such bristles have one or more of the following particular characteristics: the bristles have a non-circular cross-section, with longitudinal edges for polishing. Examples include square, triangular, a polygon with five or more sides or a bristle with spiral edges; the cross-section area of the bristles is between 0.0001 $mm^2$ and 0.0064 $mm^2$ Region 32 covers the interior surfaces of those same six teeth. These are the areas which are susceptible to tartar buildup and hence, the bristles can be more abrasive than other bristles in order to prevent or reduce the buildup of tartar. These bristles have one or more of the following particular characteristics: the bristles may include abrasive additives, such as metal or ceramic particles; the bristles may have a non-circular cross-section for added scraping; and a diameter of 0.01-0.2 mm and a length of 1-7 mm.

A third general region which includes several individual parts is shown at 34 in the FIGURE. This region is present on the interior surfaces of both side members 16 and 18 of the mouthpiece unit 12. Region 34 extends from the vertical edges 31a, 32a of regions 30 and 32, respectively, to the free ends 36 and 38 of the mouthpiece. Region 34 also extends from the upper and lower edges 39, 40, respectively, of each side member 16 and 18 a relatively short distance toward intermediate member 20, to cover the gum line region. These bristles extend at an angle of 45° in order to reach into the gum line. They are otherwise characterized with the following bristle features: the bristles could have feathered tips (extra thin and pointy), with a filament diameter of 0.01-0.05 mm, a length of 2-7 mm and, generally a circular cross-section.

Region 41, also comprising several parts, borders region 34 along the edge thereof on the interior surfaces of side member 16 and 18 and has an opposing boundary edge 42 at horizontal member 20. The bristles in these regions are perpendicular and a little shorter and stiffer in order to scrub clean the exterior vertical side surfaces of the teeth. These regions may also have special longer bristles in order to reach in between the teeth, i.e. into the interproximal spaces. These bristles have the additional characteristics of: the bristles can have feathered tips, with a bristle (filament) diameter of 0.03-0.2 mm, a length of 1-5 mm and generally a circular cross-section.

Region 44 extends along the entire length of intermediate member 20, comprising two opposing bands which abut the interior surfaces of the side members 16 and 18, leaving a space between them for another bristle region. These bristles in this region 44 clean the occlusal surfaces of the teeth and do not come into contact with the gums. These bristles have the following characteristics: a bristle diameter of 0.05-0.2 mm and a length of 1-5 mm, with a cross-section which is generally circular.

Region 46 also extends completely along the length of intermediate member 20, between the two opposing bands of region 44. The bristles in this region are also stiff, but are somewhat longer than the bristles in Region 44. These longer bristles reach the crevices of the occlusal surfaces and remove the material and any plaque that are on those surfaces. These bristles have the following bristle characteristics: the bristles are 1-3 mm longer than the bristles in Region 44, e.g. 3-8 mm, with a diameter of 0.08-0.3 mm, generally circular in cross-section.

Accordingly, a mouthpiece has been described which includes different bristles in different dental regions. In each dental region, the function of the bristles is different and therefore the characteristics of the bristles are different to best accomplish those particular functions.

Although a preferred embodiment of the invention has been disclosed for purposes of illustration, it should be understood that various changes, modifications and substitutions may be incorporated in the embodiment without departing from the spirit of the invention which is defined by the claims which follow.

The invention claimed is:

1. A mouthpiece for cleaning teeth surfaces of teeth, comprising:
    a mouthpiece carrier assembly having upper and lower channels formed by side walls separated by an intermediate member and configured to receive upper and lower teeth of a user;
    a system for driving the mouthpiece carrier assembly such that bristles mounted on teeth-facing surfaces of the mouthpiece carrier assembly contact said teeth surfaces and provide a cleaning effect therefor; and
    a plurality of bristle sections secured to the teeth-facing surfaces of the mouthpiece carrier assembly, wherein different regions of the teeth require different cleaning, the plurality of bristle sections including said bristles which have bristle characteristics adapted for cleaning of the teeth in said different teeth regions,
    wherein a first set of bristles of a first section of the plurality of bristle sections has different characteristics than a second set of bristles of a second section of the plurality of bristle sections, and wherein the intermediate member between the side walls comprises the first section and the second section.

2. The mouthpiece of claim 1, wherein the bristle sections include a section having bristles adapted for cleaning vertical side surfaces of the teeth, another section having bristles adapted for cleaning occlusal surfaces of the teeth and a further section having bristles adapted for cleaning of the gum line.

3. The mouthpiece of claim 2, including another bristle section having bristles adapted for polishing or whitening of the exterior surfaces of the front teeth.

4. The mouthpiece of claim 1, wherein the bristle sections include a section having bristles adapted for polishing or whitening the exterior surfaces of the front teeth and bristles adapted for cleaning the gum line.

5. The mouthpiece of claim 4, including another bristle section having bristles which are adapted for cleaning occlusal surfaces of the teeth.

6. The mouthpiece of claim 4, including a bristle section having bristles adapted for cleaning tartar from the interior surfaces of the front teeth.

7. The mouthpiece of claim 1, wherein the bristle sections include a section having bristles adapted for polishing or whitening of the exterior surfaces of the front teeth and a section having bristles adapted for cleaning of tartar from the interior surfaces of the front teeth.

8. The mouthpiece of claim 7, including another bristle section having bristles adapted for cleaning occlusal surfaces of the teeth.

9. The mouthpiece of claim 1, including a bristle section having bristles adapted to clean vertical surfaces of the teeth, except for the front teeth, a bristle section having bristles adapted for cleaning the gum line, and a bristle section having bristles adapted for cleaning occlusal sections of the teeth.

10. The mouthpiece of claim 1, including a bristle section having bristles adapted to clean occlusal surfaces of the teeth and another bristle section having bristles adapted for cleaning tartar from the interior surfaces of the front teeth.

11. The mouthpiece of claim 1, including bristle sections having bristles adapted for polishing or whitening of the exterior surfaces of the front teeth and bristles adapted for cleaning the occlusal surfaces of the teeth.

12. The mouthpiece of claim 1, including two bristle sections having bristles selected from the following group: (a) bristles adapted for polishing or whitening of the exterior surfaces of the front teeth; (b) bristles adapted for cleaning the vertical surfaces of the teeth; (c) bristles adapted for cleaning the occlusal surfaces of the teeth; (d) bristles adapted for cleaning of the gum line; and (e) bristles adapted for cleaning of tartar from the interior surfaces of the front teeth.

13. The mouthpiece of claim 12, including another bristle section selected from the remainder of the group of (a), (b), (c), (d) and (e).

14. The mouthpiece of claim 13, including another bristle section selected from the remainder of the group of (a), (b), (c), (d) and (e).

15. The mouthpiece of claim 14, including another bristle section selected from the remainder of the group of (a), (b), (c), (d) and (e).

16. The mouthpiece of claim 1, wherein the first section includes two edge portions of the intermediate member, and the second section is between the two edge portions, and wherein bristles of the second section are longer than bristles of the first section.

17. The mouthpiece of claim 16, wherein the bristles of the second section are 1-3 mm longer than bristles of the first section.

18. The mouthpiece of claim 1, wherein the first section and the second section extend along an entire length of intermediate member.

19. A mouthpiece for cleaning teeth surfaces of teeth, comprising:
- a mouthpiece carrier assembly having upper and lower channels formed by side walls separated by an intermediate member and configured to receive upper and lower teeth of a user;
- a system for driving the mouthpiece carrier assembly such that bristles mounted on teeth-facing surfaces of the mouthpiece carrier assembly contact said teeth surfaces and provide a cleaning effect therefor; and
- a plurality of bristle sections secured to the teeth-facing surfaces of the mouthpiece carrier assembly, wherein different regions of the teeth require different cleaning, the plurality of bristle sections including said bristles which have bristle characteristics adapted for cleaning of the teeth in said different teeth regions,
- wherein a first set of bristles of a first section of the plurality of bristle sections has different characteristics than a second set of bristles of a second section of the plurality of bristle sections,
- wherein the side walls include a first side section and a second side section, the first side section partially extending along lengths of the side walls and having bristles extending at a 45° angle having circular cross-sections with feathered tips having a reduced thickness, and the second side section extending along entire lengths of the side walls and having bristles with non-circular cross-sections.

20. A mouthpiece for cleaning teeth surfaces of teeth, comprising:
- a mouthpiece carrier assembly having upper and lower channels formed by side walls separated by an intermediate member and configured to receive upper and lower teeth of a user;
- a system for driving the mouthpiece carrier assembly such that bristles mounted on teeth-facing surfaces of the mouthpiece carrier assembly contact said teeth surfaces and provide a cleaning effect therefor;
- a plurality of bristle sections secured to the teeth-facing surfaces of the mouthpiece carrier assembly, wherein different regions of the teeth require different cleaning, the plurality of bristle sections including said bristles which have bristle characteristics adapted for cleaning of the teeth in said different teeth regions;
- wherein a first set of bristles of a first section of the plurality of bristle sections has different characteristics than a second set of bristles of a second section of the plurality of bristle sections, a third set of bristles covers exterior surfaces of front teeth of the user and have non-circular cross-section, and a fourth set of bristles that covers interior surfaces of the front teeth and include an abrasive additive, wherein the abrasive additive includes one of metal and ceramic particles.

* * * * *